United States Patent [19]
Mosley

[11] Patent Number: 5,578,020
[45] Date of Patent: Nov. 26, 1996

[54] DROP DISPENSING APPARATUS

[76] Inventor: Manuel L. Mosley, 2607 Belknap, Norman, Okla. 73071

[21] Appl. No.: 522,715

[22] Filed: Sep. 1, 1995

[51] Int. Cl.$^6$ .................................................. A61M 35/00
[52] U.S. Cl. .......................... 604/295; 604/298; 604/300
[58] Field of Search ..................................... 604/294, 295, 604/299, 300, 301; 222/207, 214, 420

[56]   References Cited

U.S. PATENT DOCUMENTS

| | | | |
|---|---|---|---|
| 2,237,213 | 4/1941 | Brown | 221/102 |
| 2,734,665 | 2/1956 | Flamm | 604/295 |
| 2,811,283 | 10/1957 | Bowen | 222/109 |
| 2,920,624 | 1/1960 | Lerner et al. | 128/233 |
| 3,366,284 | 1/1968 | Marona et al. | 222/211 |
| 3,552,605 | 1/1971 | Hein | 222/207 |
| 4,111,200 | 9/1978 | Sbarra et al. | 128/233 |
| 4,792,334 | 12/1988 | Py | 604/295 |
| 4,834,727 | 5/1989 | Cope | 604/300 |
| 4,925,065 | 5/1990 | Golias | 222/189 |
| 4,927,062 | 5/1990 | Walsh | 222/420 |
| 5,007,905 | 4/1991 | Bauer | 604/295 |
| 5,261,571 | 11/1993 | Goncalves | 222/214 |

*Primary Examiner*—Michael J. Milano
*Assistant Examiner*—David J. Cho

[57]   ABSTRACT

An eye drop dispenser having a dropper tube and a dispensing sleeve. The dropper tube has a liquid reservoir portion and has a dispensing end with a dropper orifice. At least part of the reservoir portion of the dropper tube is made of a resilient material. The dispensing sleeve has a sleeve portion which circumscribes the dropper tube and a pair of legs which extend beyond the dispensing end of the dropper tube. The legs of the dispensing sleeve are adapted to fit against upper and lower orbital areas of an eye in order to support the dropper orifice over the eye. A pair of squeeze members is carried by the dispensing sleeve. Each squeeze member has a rigid squeeze surface disposed toward the dropper tube in an opposing relationship to the other squeeze surface. In use, the eye drop dispenser is positioned with the legs of the dispensing sleeve against upper and lower orbital areas of the eye. Then the dispensing sleeve is squeezed such that the squeeze members deform the dropper tube inwardly to force a drop of liquid through of the dropper orifice of the dropper tube and into the eye.

20 Claims, 3 Drawing Sheets

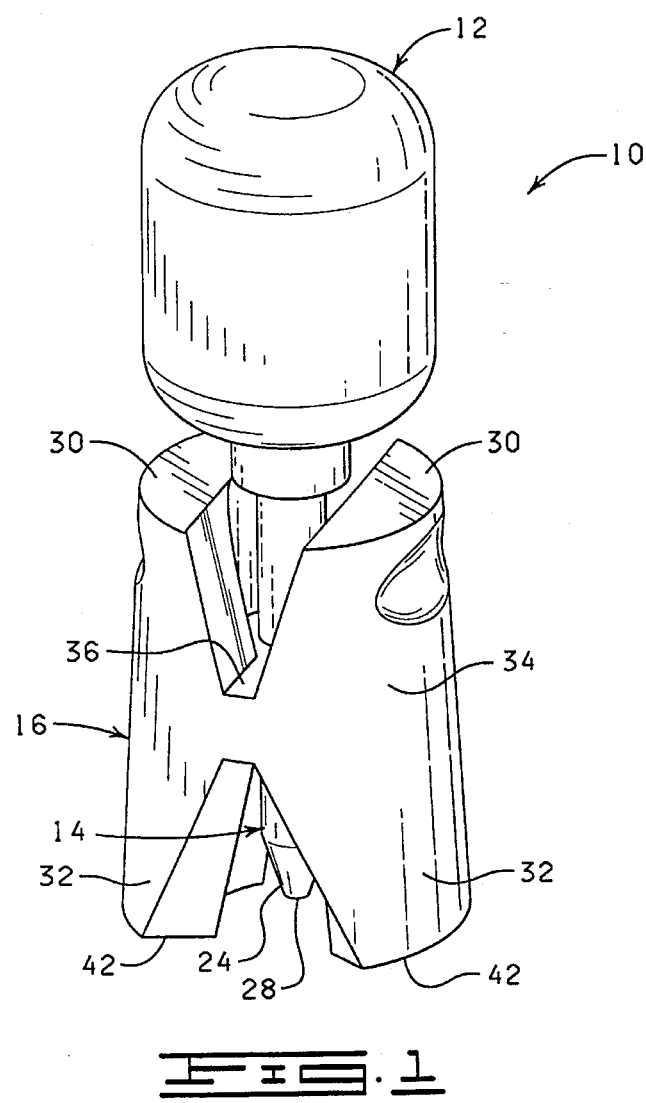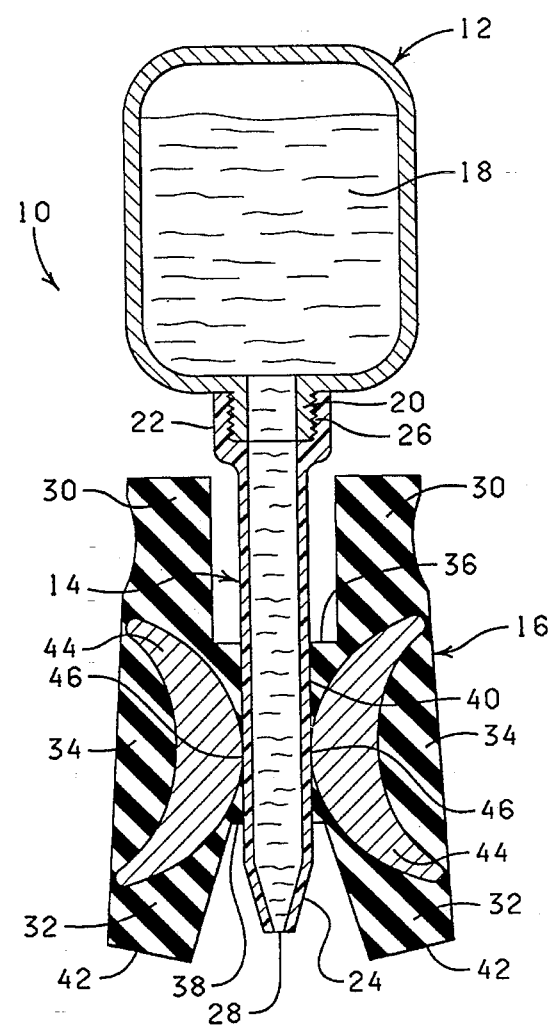

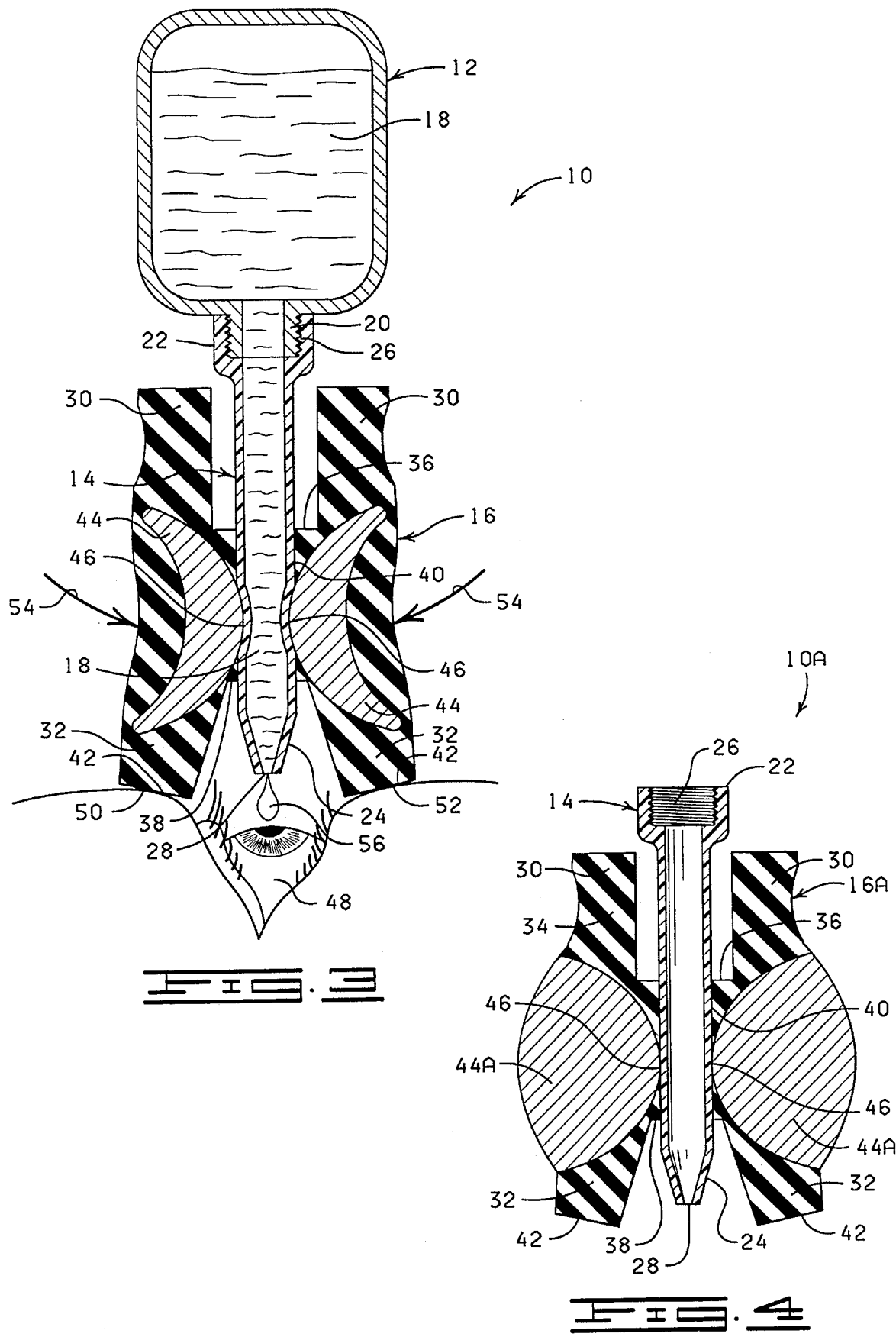

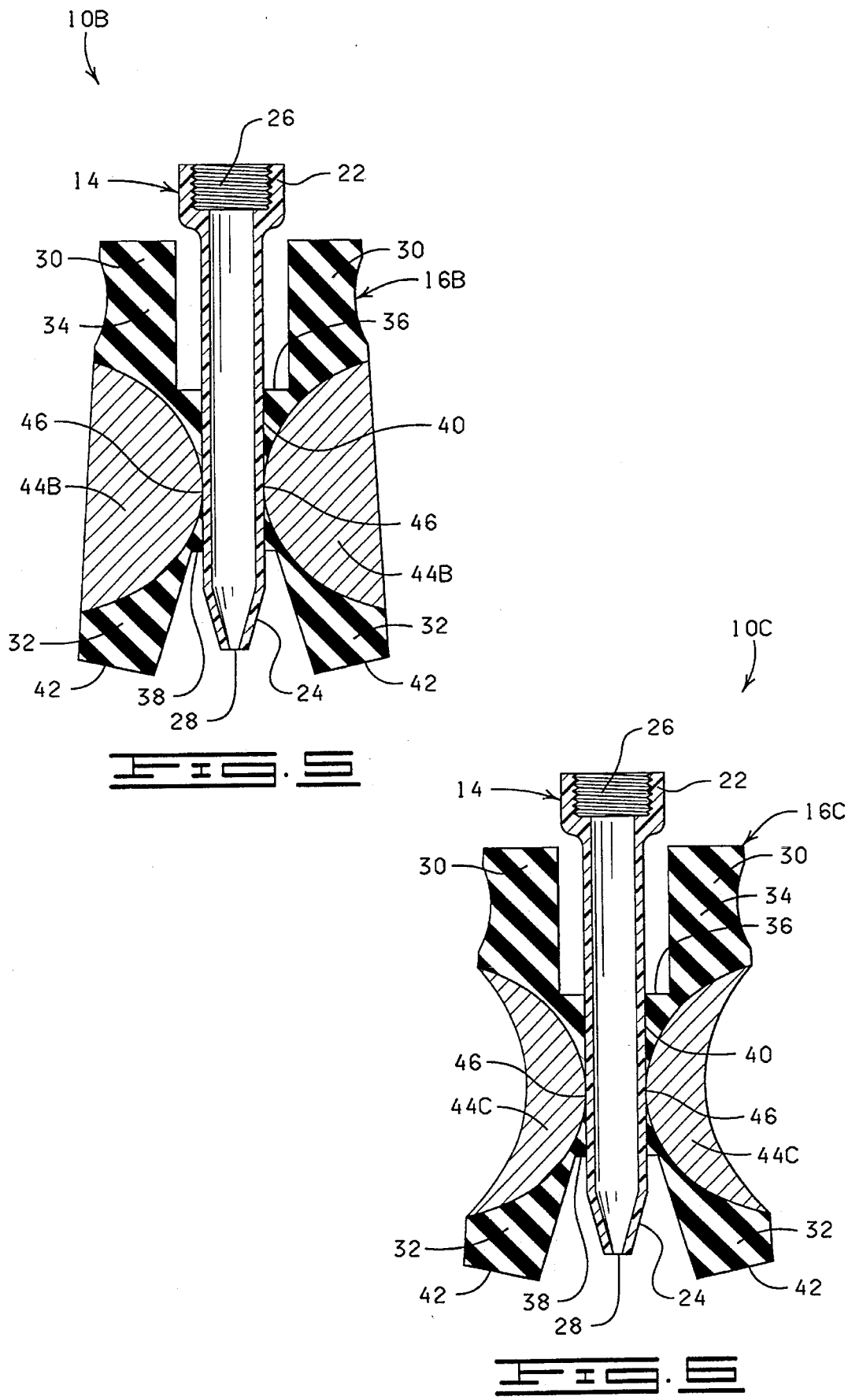

DROP DISPENSING APPARATUS

BACKGROUND OF THE INVENTION

1. Field of the Invention

The present invention relates generally to devices for dispensing drops and particularly, but not by way of limitation, to an apparatus for accurately administering uniformly measured drops into the eye.

2. Description of Related Art

Various types of eye drop dispensing devices are known in the art. For example, U.S. Pat. No. 4,111,200 issued to Sbarra et al. discloses an eye drop dispenser comprising a cup-like part which is snapped onto a squeeze bottle.

U.S. Pat. No. 4,834,727 issued to Cope discloses an eye dropper bottle attachment. This device includes a ring stand which supports a dispenser bottle over the eye.

U.S. Pat. No. 5,007,905 issued to Bauer discloses an eye drop applicator. This particular apparatus comprises a cup having a lip portion to fit around an eyeball to keep the eye lid open.

SUMMARY OF THE INVENTION

The present invention is an eye drop dispenser comprising a dropper tube and a dispenser member. The dropper tube is hollow for containing a liquid and has a dispensing orifice for drop-wise release of the liquid. The dispenser member has a sleeve portion and a base portion.

The sleeve portion of the dispenser member surrounds the dropper tube and has a pair of convex surfaces which oppose one another and impinge against the dropper tube. The base portion of the dispenser member extends past the dispenser orifice of the dropper tube such that the base portion may be situated against the orbital area around an eye and thereby support the dispensing orifice in proper position for releasing drops from the dropper tube into the eye.

The dropper tube is inwardly flexible at least where the convex surfaces of the dispenser member are located. Squeezing pressure on the sleeve portion of the dispenser member causes the convex surfaces of the dispenser member to pinch the dropper tube and force a drop of liquid through the dispenser orifice of the dropper tube and into the eye.

One object of the present invention is to provide an eye drop dispenser which ensures proper positioning for administering eye drops into the eye.

Another object of the present invention is to provide an eye drop dispenser which releases uniformly measured drops.

Yet another object of the present invention is to provide an eye drop dispenser which aids in releasing one drop at a time so that the desired number of drops may be administered into the eye.

Other objects, features and advantages of the present invention are apparent from the following detailed description when read in conjunction with the accompanying drawings and appended claims.

BRIEF DESCRIPTION OF THE DRAWINGS

FIG. 1 is a perspective view of an eye drop dispenser constructed in accordance with the present invention.

FIG. 2 is a sectional view of the eye drop dispenser shown in FIG. 1.

FIG. 3 is the same view as FIG. 2 but shows a drop being administered into an eye by the eye drop dispenser.

FIG. 4 is a sectional view of another preferred embodiment of the eye drop dispenser showing, the squeeze members of the dispenser sleeve having a biconvex shape.

FIG. 5 is a sectional view of another preferred embodiment of the eye drop dispenser showing, the squeeze members of the dispenser sleeve having a plano-convex shape.

FIG. 6 is a sectional view of another preferred embodiment of the eye drop dispenser showing, the squeeze members of the dispenser sleeve having a convexo-concave shape.

DETAILED DESCRIPTION OF THE PREFERRED EMBODIMENTS

Referring to the drawings in general, and to FIGS. 1 and 2 in particular, shown therein and designated by the general reference numeral 10 is an eye drop dispenser, which includes a vial 12, a dropper tube 14 and a dispensing sleeve 16.

Typically, the vial 12 is any plastic container suitable for holding a liquid 18. However, the vial 12 may be made of glass or any other material used for conventional medicine bottles. The vial 12 has a threaded neck 20 for attachment of the dropper tube 14 or a cap (not shown). Further, the vial 12 may be adapted for snap-on attachment or any other conventional attachment of a cap or the dropper rather than the screw-on type shown in the drawing figures.

The vial 12 may be constructed of a flexible, resilient material like any of the substances used for conventional squeeze bottles. However, for the purposes of the present invention, the vial 12 may be may be constructed of a rigid material, such as glass or hard plastic.

The dropper tube 14 has a first end 22 and a second or dispensing end 24. The first end 22 of the dropper tube 14 is open to receive liquid to be dispensed in a drop-wise manner. Further, the first end 22 of the dropper tube 14 has threads 26 so that the dropper tube 14 may be attached to the vial 12 or to a cap (not shown).

As mentioned previously, the vial 12 may be provided with snap-on or other attachment means. In such case, the first end 22 of the dropper tube 14 would have complementary attachment means rather than the threads 26. Of course, the connection between the vial 12 and the dropper tube 14 should be liquid-tight.

The dropper tube 14 is hollow to contain a volume of liquid to be used as eye drops. The dispensing end 24 of the dropper tube 14 has an orifice 28 for releasing a drop of liquid at one time from the dropper tube 14.

The orifice 28 of the dropper tube 14 should be sized and shaped such that the particular liquid in the dropper tube 14 does not drop-release from the orifice 28 unless external pressure is applied. Thus, the size and shape of the dropper tube orifice 28 should be appropriate for the viscosity of the particular liquid in the dropper tube 14.

As shown in FIGS. 1 and 2, the dispensing end 24 of the dropper tube 14 is typically frustoconical in shape. However, the dispensing end 24 of the dropper tube 14 may be any suitable shape known in the art for releasing a liquid in drop-wise fashion.

The dropper tube 14 may be constructed of any rigid, semi-rigid or semi-flexible plastic material. However, for reasons which will become apparent hereinafter, at least a portion of the dropper tube 14 should be sufficiently resilient to flex inward when subjected to a squeezing force and to return to its original shape when the squeezing force is removed.

The dispensing sleeve 16 comprises a pair of collars 30, a pair of legs 32, and a sleeve portion 34 having a first end 36 and a second end 38. A bore 40 sized to receive the dropper tube 14 extends from the first end 36 to the second end 38 of the sleeve portion 34 of the dispensing sleeve 16.

The collars 30 extend angularly outward from the first end 36 of the sleeve portion 34 of the dispensing sleeve 16. As best seen in FIG. 1, the two collars 30 are diametrically opposed to one another.

In similar fashion, the legs 32 extend angularly outward from the second end 38 of the sleeve portion 34. It should be appreciated that each one of the legs 32 generally aligns with a respective one of the collars 30 and that each space between the collars 30 generally aligns with a corresponding space between the legs 32.

As best illustrated by FIG. 2, the legs 32 have lengths to extend beyond the orifice 28 of the dropper tube 14. Further, each one of the legs 32 has a curved base surface 42 which is sized and shaped to fit against a corresponding upper or lower orbital area around an eye.

It should be appreciated that the shapes of the collars 30, legs 32 and sleeve portion 34 provide an excellent contour for gripping the sleeve portion 34 of the drop dispenser 10 between the forefinger and thumb. In particular, the collars 30 help prevent accidental dropping of the drop dispenser 10.

Typically, the dispensing sleeve 16 is made of a flexible, pliable elastomeric material, except for a pair of squeeze members 44. The dispensing sleeve 16 may be molded in one piece or may be constructed in any other conventional manner.

As shown in FIG. 2, the squeeze members 44 oppose one another and are located in an area of the dispensing sleeve 16 extending from the sleeve portion 34 into the corresponding one of the legs 32. Each one of the squeeze members 44 has a squeeze surface 46 which is disposed toward the dropper tube 14.

The squeeze members 44 may be provided in any of a wide variety of shapes. In one preferred embodiment illustrated by FIG. 2, the squeeze members 44 have a concavo-convex shape.

The squeeze members 44 should be constructed of a substantially rigid material, such as metal, hard plastic, glass, ceramic, polyethylene, polypropylene, hard natural or synthetic rubber or any other suitably rigid material known in the art. The squeeze surfaces 46 of the squeeze members 44 should be rigid enough to cause inward deformation of the dropper tube 14 when the dispensing sleeve 16 is squeezed. It is also advantageous for the squeeze members 44 to be made of a material which is easily imbedded in or adhered to the material of the dispensing sleeve 16.

Typically, the squeeze surfaces 46 of the squeeze members 44 are substantially identical in size and shape. However, the squeeze members 44 may be different in size or shape to achieve particular drop-releasing characteristics for the dispenser 10.

Use of the Drop Dispenser

Use of the eye drop dispenser 10 is best understood with reference to FIG. 3. The dispenser 10 is placed over an eye 48 with the base surface 42 of one leg 32 against an upper orbital area 50 around the eye 48 and with the base surface 42 of the other leg 32 against a lower orbital area 52 around the eye 48.

Disposing the legs 32 against the orbital areas 50 and 52 accurately locates the orifice 28 of the dropper tube 14 over the eye 48. Then the dispensing sleeve 16 is squeezed as indicated by arrows 54.

Squeezing the sleeve portion 34 of the dispensing sleeve 16 causes the squeeze members 44 to put inward pressure on the wall of the dropper tube 14. In response to this inward pressure, the wall of the dropper tube 14 flexes inward to force a drop 56 of liquid 18 through the orifice 28, out of the dropper tube 14, and into the eye 48.

When the squeeze pressure is removed, the resiliency of the elastomeric dispensing sleeve 16 causes the dispensing sleeve 16 to return to its normal shape. As a result, the squeeze members 44 and the wall of the dropper tube 14 return to their normal positions, which are shown in FIG. 2.

Embodiments Shown in FIGS. 4 through 6

Referring to FIG. 4, shown therein and designated by reference character 10A is another preferred embodiment of the drop dispenser. The dispenser 10A includes a dispensing sleeve 16A which carries a pair of biconvex squeeze members 44A.

With reference to FIG. 5, shown therein and designated by reference character 10B is yet another preferred embodiment of the drop dispenser. The dispenser 10B comprises a dispensing sleeve 16B which carries a pair of plano-convex squeeze members 44B.

Referring to FIG. 6, shown therein and designated by reference character 10C is still another preferred embodiment of the drop dispenser. The drop dispenser 10C includes a dispensing sleeve 16C which carries a pair of concavo-convex squeeze members 44C having exposed concave surfaces.

It may be seen from these embodiments that the squeeze members may be provided in a wide variety of shapes and may be partially or wholly embedded within the dispensing sleeve. Although it is preferred that the squeeze members have a convex squeeze surface 46, the squeeze surfaces may be any shape consistent with their intended purpose. For example, the squeeze members may be spherical, ovate, cylindrical, pyramidic, cube-shaped, rectangular, block-shaped or many other shapes.

It should be appreciated that any of the embodiments disclosed hereinabove may be constructed and used without the vial 12. In such a manner, liquid may be placed directly into the dropper tube 14. A screw-on or snap-on cap or plug (not shown) may be secured to the first end 22 of the dropper tube 14 to close that end of the dropper tube 14. Further, the dispensing end 24 of the dropper tube 14 may be modified to receive a screw-on or snap-on cap or the like to cover the dropper orifice 28 when the drop dispenser is not in use.

From the above discussion, it should be apparent that the rigidity, position and shape of the squeeze members 44, 44A, 44B or 44C allow precise control of squeeze pressure on the dropper tube 14. When the dropper tube 14 is squeezed, a metered amount of medicine is dispensed. Thus, the present invention achieves a high degree of uniformity in the dispensing of drops. This precise control of squeeze pressure and the accurate positioning of the dropper orifice 28 afforded by the dispensing member legs 32 provides for extremely accurate administration of the desired number of drops into the eye.

It should also be understood that the construction of the present invention allows air to replace dispensed liquid. In this manner, a vacuum does not develop above the liquid to adversely affect the ease with which drops can be dispensed from the dropper tube 14.

Changes may be made in the combinations, operations and arrangements of the various parts and elements described herein without departing from the spirit and scope of the invention as defined in the following claims.

What is claimed is:

1. A dispenser for administering a metered amount of liquid into a target, the dispenser comprising:

a dropper tube having a first end and a dispensing end, at least a portion of the dropper tube being deformable by finger pressure; and a flexible dispensing sleeve disposed about the dropper tube, the dispensing sleeve having a support end extending past the dispensing end of the dropper tube for supporting the dropper tube over the target, the dispensing sleeve being engaged with the deformable portion of the dropper tube such that the application of a squeeze pressure to the dispenser sleeve causes the dropper tube to be deformed inwardly so as to cause the release of the metered amount of a liquid disposed in the dropper tube from the dispensing end of the dropper tube and into the target.

2. The dispenser of claim 1 wherein the dispensing end of the dropper tube is frustoconical in shape.

3. The dispenser of claim 1 wherein the dispensing sleeve is molded in one piece.

4. The dispenser of claim 1 wherein the dispensing sleeve is an elastomeric material.

5. The dispenser of claim 1 further comprising:

a vial attached to the first end of the dropper tube and communicating with the dropper tube to supply liquid to the dropper tube.

6. The dispenser of claim 5 further comprising:

means for removably securing the vial to the dropper tube in a fluid-tight arrangement.

7. An eye drop dispenser, comprising:

a dropper tube having a first end and a dispensing end, at least a portion of the dropper tube being deformable; and a flexible dispensing sleeve disposed about the dropper tube, the dispensing sleeve having a support end extending past the dispensing end of the dropper tube for supporting the dropper tube over an eye, the dispensing sleeve being engaged with the deformable portion of the dropper tube such that the application of a squeeze pressure to the dispenser sleeve causes the dropper tube to be deformed inwardly so as to cause the release of a metered amount of a liquid disposed in the dropper tube from the dispensing end of the dropper tube and into the eye.

8. An eye drop dispenser, comprising:

a dropper tube having a first end and a dispensing end, at least a portion of the dropper tube being deformable;

a flexible dispensing sleeve disposed about the dropper tube, the dispensing sleeve having a support end extending past the dispensing end of the dropper tube for supporting the dropper tube over an eye; and a pair of squeeze members embedded in the dispensing sleeve, each of the squeeze members having a substantially rigid squeeze surface disposed toward the deformable portion of the dropper tube such that the application of a squeeze pressure to the dispenser sleeve causes the squeeze members in the dispenser sleeve to compress the dropper tube so as to cause the release of a metered amount of a liquid disposed in the dropper tube from the dispensing end of the dropper tube and into the eye.

9. The eye drop dispenser of claim 8 wherein the squeeze surfaces of the squeeze members are diametrically opposed to one another.

10. The eye drop dispenser of claim 8 wherein each one of the squeeze members has a convex surface disposed toward the dropper tube.

11. The eye drop dispenser of claim 10 wherein the convex surface of each one of the squeeze members is in contact with the dropper tube.

12. The eye drop dispenser of claim 8 wherein the dispensing sleeve is molded in one piece.

13. The eye drop dispenser of claim 8 wherein the dispensing sleeve is an elastomeric material.

14. The eye drop dispenser of claim 8 further comprising:

a vial attached to the first end of the dropper tube and communicating with the dropper tube to supply liquid to the dropper tube.

15. The eye drop dispenser of claim 14 further comprising:

means for removably securing the vial to the dropper tube in a fluid-tight arrangement.

16. The eye drop dispenser of claim 8 wherein the dispensing end of the dropper tube is frustoconical in shape.

17. The eye drop dispenser of claim 8 wherein each one of the squeeze members is concavo-convex.

18. The eye drop dispenser of claim 8 wherein each one of the squeeze members is plano-convex.

19. The eye drop dispenser of claim 8 wherein the dropper tube is a resilient plastic material.

20. The eye drop dispenser of claim 8 wherein the support end of the dispensing sleeve comprises:

a pair of legs sized and shaped such that the dispensing sleeve supports the dispensing end of the dropper tube over the eye with one of the legs resting against an orbital area above the eye and the other one of the legs resting against an orbital area below the eye.

* * * * *